US007290544B1

(12) United States Patent
Särelä et al.

(10) Patent No.: US 7,290,544 B1
(45) Date of Patent: Nov. 6, 2007

(54) ARRANGEMENT IN CONNECTION WITH FEEDBACK CONTROL SYSTEM

(75) Inventors: Antti Särelä, Espoo (FI); Mario Loncar, Ekerö (SE)

(73) Assignee: GE Healthcare Finland Oy (FI)

( * ) Notice: Subject to any disclaimer, the term of this patent is extended or adjusted under 35 U.S.C. 154(b) by 0 days.

(21) Appl. No.: 09/857,682

(22) PCT Filed: Dec. 3, 1999

(86) PCT No.: PCT/FI99/01007

§ 371 (c)(1),
(2), (4) Date: Sep. 4, 2001

(87) PCT Pub. No.: WO00/33904

PCT Pub. Date: Jun. 15, 2000

(30) Foreign Application Priority Data

Dec. 8, 1998 (FI) .................................... 982653

(51) Int. Cl.
| *A61M 16/00* | (2006.01) |
| *A61B 9/00* | (2006.01) |
| *G08B 3/00* | (2006.01) |
| *G08B 5/00* | (2006.01) |
| *A62B 27/00* | (2006.01) |

(52) U.S. Cl. ............................. 128/202.22; 128/203.14
(58) Field of Classification Search .......... 128/203.12, 128/203.14, 203.26, 203.27, 203.28, 203.25, 128/202.22, 204.21, 204.23
See application file for complete search history.

(56) References Cited

U.S. PATENT DOCUMENTS 4,366,821 A * 1/1983 Wittmaier et al. .......... 600/532

(Continued)

FOREIGN PATENT DOCUMENTS

| EP | 720858 | 7/1996 |
| EP | 835672 | 4/1998 |
| EP | 968735 | 1/2000 |
| GB | 1294808 | 11/1972 |
| WO | 87/06142 | 10/1987 |
| WO | 96/03174 | 2/1996 |
| WO | 98/31282 | 7/1998 |

OTHER PUBLICATIONS

"*Closed-loop control of blood pressure, ventilation, and anesthesia delivery*", Dwayne R. Westenskow, International Journal of Clinical Monitoring and Computing, vol. 4, 1987, pp. 69-74.

(Continued)

*Primary Examiner*—Michael J. Hayes
*Assistant Examiner*—Michael G. Mendoza
(74) *Attorney, Agent, or Firm*—Andrus, Sceales, Starke & Sawall, LLP

(57) ABSTRACT

The invention relates to an arrangement in connection with a feedback control system, the arrangement comprising a controllable device (10), a measuring device (7), a controlling device (9) and a user interface by which the controlling device (9) can be monitored by means of set values. The measuring device (7) is adapted to measure a measuring value (8) from a measuring point, which measuring value is dependent on the operation of the controllable device and the controlling device (9) is adapted to monitor the controllable device (10) on the basis of the measuring value and set values. To improve safety, the arrangement comprises means (15*a*, 15*b*, 15*c*) adapted to feed a reference signal (16) to the measuring device (7) periodically. The controlling device (9) is adapted to compare a measuring value (18) obtained from the reference signal with the real reference value (17) of the reference signal and adapted to take a safety measure when the measuring value (18) and the real reference value (17) differ substantially from each other.

23 Claims, 2 Drawing Sheets

U.S. PATENT DOCUMENTS

| | | | |
|---|---|---|---|
| 4,502,490 A | | 3/1985 | Evans et al. |
| 4,651,729 A | * | 3/1987 | Rae .................. 128/203.14 |
| 4,897,184 A | | 1/1990 | Shouldice et al. |
| 4,934,358 A | * | 6/1990 | Nilsson et al. ......... 128/200.23 |
| 4,972,842 A | * | 11/1990 | Korten et al. ............ 600/529 |
| 4,986,268 A | * | 1/1991 | Tehrani ................ 128/204.22 |
| 5,057,822 A | * | 10/1991 | Hoffman .................... 340/611 |
| 5,072,737 A | * | 12/1991 | Goulding .................. 600/531 |
| 5,094,235 A | * | 3/1992 | Westenskow et al. .. 128/204.22 |
| 5,199,424 A | * | 4/1993 | Sullivan et al. ........ 128/204.18 |
| 5,245,995 A | * | 9/1993 | Sullivan et al. ........ 128/204.23 |
| 5,320,092 A | * | 6/1994 | Ryder ................. 128/202.22 |
| 5,320,093 A | * | 6/1994 | Raemer ............... 128/203.12 |
| 5,331,995 A | * | 7/1994 | Westfall et al. .............. 137/8 |
| 5,363,842 A | * | 11/1994 | Mishelevich et al. .... 128/200.14 |
| 5,365,922 A | * | 11/1994 | Raemer ................ 128/204.23 |
| 5,522,382 A | * | 6/1996 | Sullivan et al. ........ 128/204.23 |
| 5,558,083 A | * | 9/1996 | Bathe et al. ........... 128/203.12 |
| 5,590,651 A | * | 1/1997 | Shaffer et al. ............. 600/532 |
| 5,626,131 A | * | 5/1997 | Chua et al. ............ 128/204.23 |
| 5,730,119 A | * | 3/1998 | Lekholm ................ 128/200.24 |
| 5,732,694 A | | 3/1998 | Bathe et al. |
| 5,752,509 A | * | 5/1998 | Lachmann et al. .... 128/204.23 |
| 5,865,174 A | * | 2/1999 | Kloeppel ............... 128/204.23 |
| 5,931,160 A | * | 8/1999 | Gilmore et al. ........ 128/204.21 |
| 6,131,571 A | * | 10/2000 | Lampotang et al. ... 128/204.21 |
| 6,158,432 A | * | 12/2000 | Biondi et al. .......... 128/204.21 |
| 6,398,739 B1 | * | 6/2002 | Sullivan et al. ............. 600/529 |
| 6,463,930 B2 | * | 10/2002 | Biondi et al. .......... 128/204.21 |
| 6,892,726 B1 | * | 5/2005 | Heinonen et al. ...... 128/202.22 |

OTHER PUBLICATIONS

"A model for technology assessment as applied to closed loop infusion systems", Michael Jastremski et al., Critical care Medicine, vol. 23, No. 10, 1995, pp. 1745-1755.

"Development of a portable closed-loop atracurium infusion system: systems methodology and safety issues", David G. Mason et al., International Journal of Clinical Monitoring and Computing, vol. 13, 1997, pp. 243-252.

* cited by examiner

ARRANGEMENT IN CONNECTION WITH FEEDBACK CONTROL SYSTEM

CROSS REFERENCE TO RELATED APPLICATION

The present application is the U.S. national stage application of International Application PCT/FI99/01007, filed Dec. 3, 1999, which international application was published on Jun. 15, 2000 as International Publication WO 00/33904 in the English language. The International Application claims the priority of Finnish Patent Application 982653, filed Dec. 8, 1998.

SUMMARY OF THE INVENTION

The invention relates to an arrangement in connection with a feedback control system, the arrangement comprising a controllable device, a measuring device, a controlling device and a user interface by which the controlling device can be monitored by means of set values, whereby the measuring device is adapted to measure a measuring value from a measuring point, which measuring value is dependent on the operation of the controllable device, and the controlling device is adapted to monitor the controllable device on the basis of the measuring values and set values.

A basic requirement set for devices used in patient care is that they are safe and operationally reliable in the normal use of the device, in fault situations unintentionally caused by a user or in any one-fault situation of the device.

As examples of the above mentioned devices for patient care, ventilators and anaesthesia machines used in intensive care and anaesthesia can be mentioned. A patient is normally connected to a device used in patient care, e.g. to anaesthesia machine and ventilator, by means of a patient circuit. From the patient circuit there is a measuring connection to a monitor which monitors the condition of the patient. Using measuring information on the condition of the patient that the monitor provides a healthcare person supervises the condition of the patient and adjusts set values of the device used in patient care so that the measuring information corresponds to the desired value of the moment.

Characteristic of the control described above is that measuring values are only indirectly affected through the set values of the device used in patient care, and also that the control has a long-term effect. Some of these indirect pairs of measuring values and set values are listed in the table below by way of example.

| Measuring value | Operative set value |
| --- | --- |
| Anaesthetic gas concentration of respiration | Anaesthetic concentration of anaesthesia machine vaporizer and gas flow of gas mixer |
| Oxygen concentration of respiration | Oxygen flow of gas mixer |
| Nitrous oxide concentration of respiration | Nitrous oxide flow of gas mixer |
| Carbon dioxide concentration of respiration | Minute ventilation of ventilator |
| Patient airway pressure | Respiration volume of ventilator |

Dependence between measuring parameters and the operative set value may include several control systems within each other. For example, blood pressure can be regulated by means of anaesthetic concentration of exhalation, whereby the anaesthetic concentration in turn is regulated by means of the anaesthetic concentration of anaesthetic vaporizer of the gas mixer according to the table above.

Due to indirectness and a long time constant, the exact adjustment of measuring values is slow and difficult, which leads to variation in patient values, and this in turn may have harmful effects on the end result of nursing.

To improve the situation, a variety of solutions have been suggested for automatizing a control loop. In such a system, a controller, instead of a person taking care of the patient, closes the control system between the measuring value and the set value of the device for patient care, which controller is capable of considering prevailing indirectnesses and the effect of the control time constant and thus of automatically optimising the set value. With such a system in use, a healthcare person only needs to set a desired value into the control system. For example U.S. Pat. No. 5,094,235 describes a similar automatized control system as above. In addition, several examples can be found in literature which describe the superiority of an automatized control system over a healthcare person in achieving and maintaining patient values. As an example, the publication Westenskow D., Closed loop control of blood pressure, ventilation and anesthesia delivery, Int J. Clin. Monitoring and Computing 4: 69-74, 1987 can be mentioned. A summary of such potential control systems is given in the publication A model for technology assessment as applied to closed loop infusion systems, Critical Care Medicine, Vol 23, No 10, 1995.

In spite of the above factors, feedback control systems have not become more common in nursing environments. One reason why the solutions, practicable as such, have remained at exploratory and experimental stages are the above mentioned safety and reliability requirements set for the equipment. An automatic feedback complicates the system considerably and brings new possibilities of fault situations, the existence of which should be taken into account when implementing the equipment. Safety issues have been taken into account e.g. in the control system of an infusion system affecting muscle relaxation, David G. Mason et al., Development of a portable closed-loop atracurium infusion system: systems methodology and safety issues, Int. J. Clin. Monitoring and Computing 13: 243-252, 1997. This research introduces methods for equipment planning, which substantially improve the safety of the system.

As stated above, a safety risk is substantially present in the feedback control system, as only devices for patient care are planned to cope with one-fault situations in operational environments. Basically, the user is often responsible for the reliability of a measurement result given by the monitor. Measuring equipment and the above experimental control systems have not been planned such that one-fault situations would not create a danger for a patient.

BRIEF DESCRIPTION OF THE INVENTION

The object of the invention is to provide an arrangement by which the prior art disadvantages can be eliminated. This is achieved by the arrangement according to the invention, characterized in that the arrangement comprises means adapted to feed a reference signal to the measuring device periodically and that the controlling device is adapted to compare the measuring value obtained on the basis of the reference signal with the real reference value of the reference signal and adapted to take a safety measure when the measuring value and the reference value differ substantially from each other.

Above all the invention provides the advantage that measuring devices on the market do not have to be redesigned for one-fault situations. A fault is recognised by an external controller which automatically checks the operation of the measuring device as a whole by means of reference measurement. The automatic checking can usually be performed by employing a very simple technique. An independent reference source is also easily available in the system. Due to simplicity, the actual controller can be straightforwardly planned against one-fault situations, and the end result is advantageous in all respects.

BRIEF DESCRIPTION OF THE DRAWING

In the following the invention will be described in greater detail by means of examples illustrated in the attached drawing, in which.

DETAILED DESCRIPTION OF THE INVENTION

Figure 1:
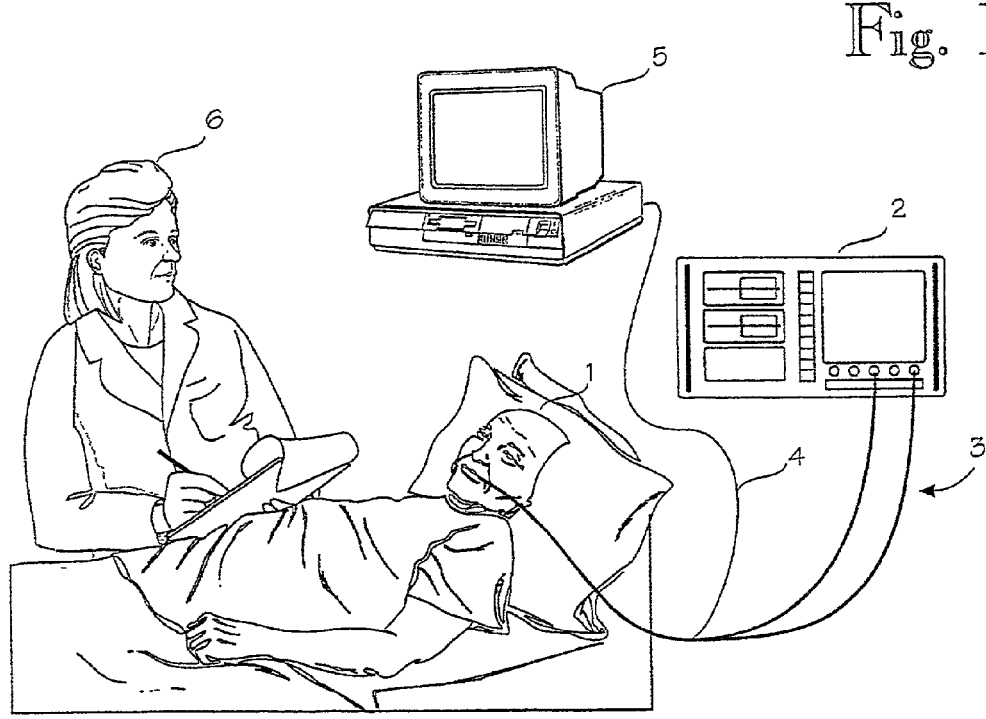
FIG. 1 shows a schematic view of an operational environment of equipment used in patient care.

FIG. 1 shows a schematic view of an operational environment of equipment used in patient care. A patient 1 is connected to a device used in patient care, which, in the example of FIG. 1, is a combination of a gas mixer and ventilator 2. The patient is connected by means of a patient circuit 3. From the patient circuit 3 there is a measuring connection 4 to a monitor 5 which monitors the condition of the patient. A healthcare person 6 supervises the condition of the patient on the basis of the measuring information on the condition of the patient provided by the monitor 5 and, when necessary, adjusts set values of the device used in patient care such that the measuring information corresponds to the desired value of the moment, as explained above.

Figure 2:
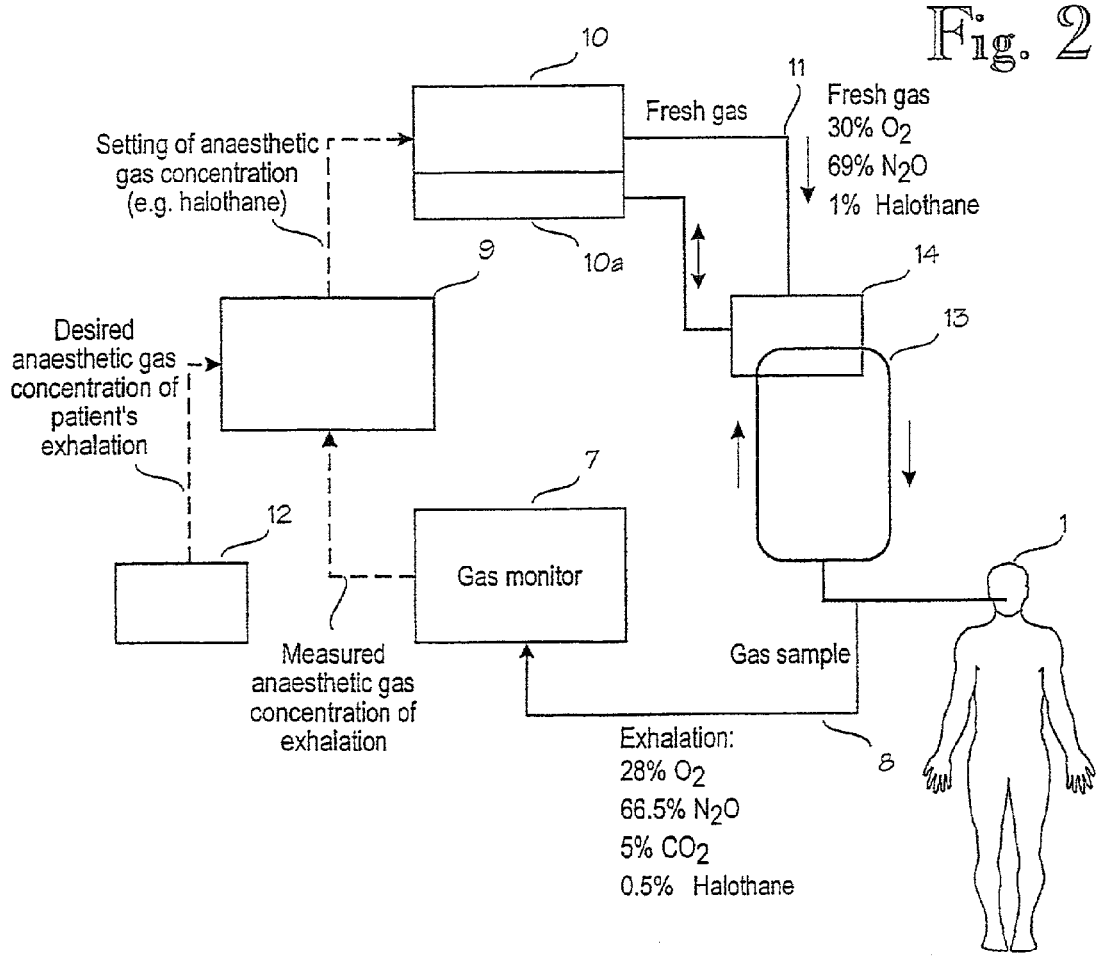
FIG. 2 shows a diagram of an example of an automatic control arrangement of a gas dispenser in an anaesthesia machine.

FIG. 2 for its part shows a control system, in which a gas dispenser of an anaesthesia machine is automatically controlled on the basis of a signal given by breathing gas measurement of the monitor. If, as a result of a fault situation, a gas monitor 7 measures a lower anaesthetic gas concentration 8 than it in fact is or does not measure it at all, a controller 9 sets a gas dispenser 10 to produce a higher anaesthetic gas concentration than at actually should be according to a user 12. This leads to an overdose of the anaesthetic and thus to a dangerous situation. Gas concentrations shown in FIG. 2 are only exemplificational values. In FIG. 2, a patient circuit is indicated by the reference number 13, a CO2 absorber by the reference number 14 and a ventilator by the reference number 10a. As in the example of FIG. 1, a patient is marked with the a reference number 1.

In principle, the system of FIG. 2 operates in the following way. While a patient is under treatment, the gas dispenser 10 feeds a desired gas mixture to the patient and the gas monitor 7 measures the anaesthetic gas concentration and informs the controller 9 of it. The controller 9 adjusts the setting of the anaesthetic gas concentration in order to achieve the desired end result. The user 12 has naturally set a desired anaesthetic gas concentration of the patient's exhalation to the controller 9.

The control system of FIG. 2 has the disadvantages described above, which have been eliminated by the invention.

Figure 3:
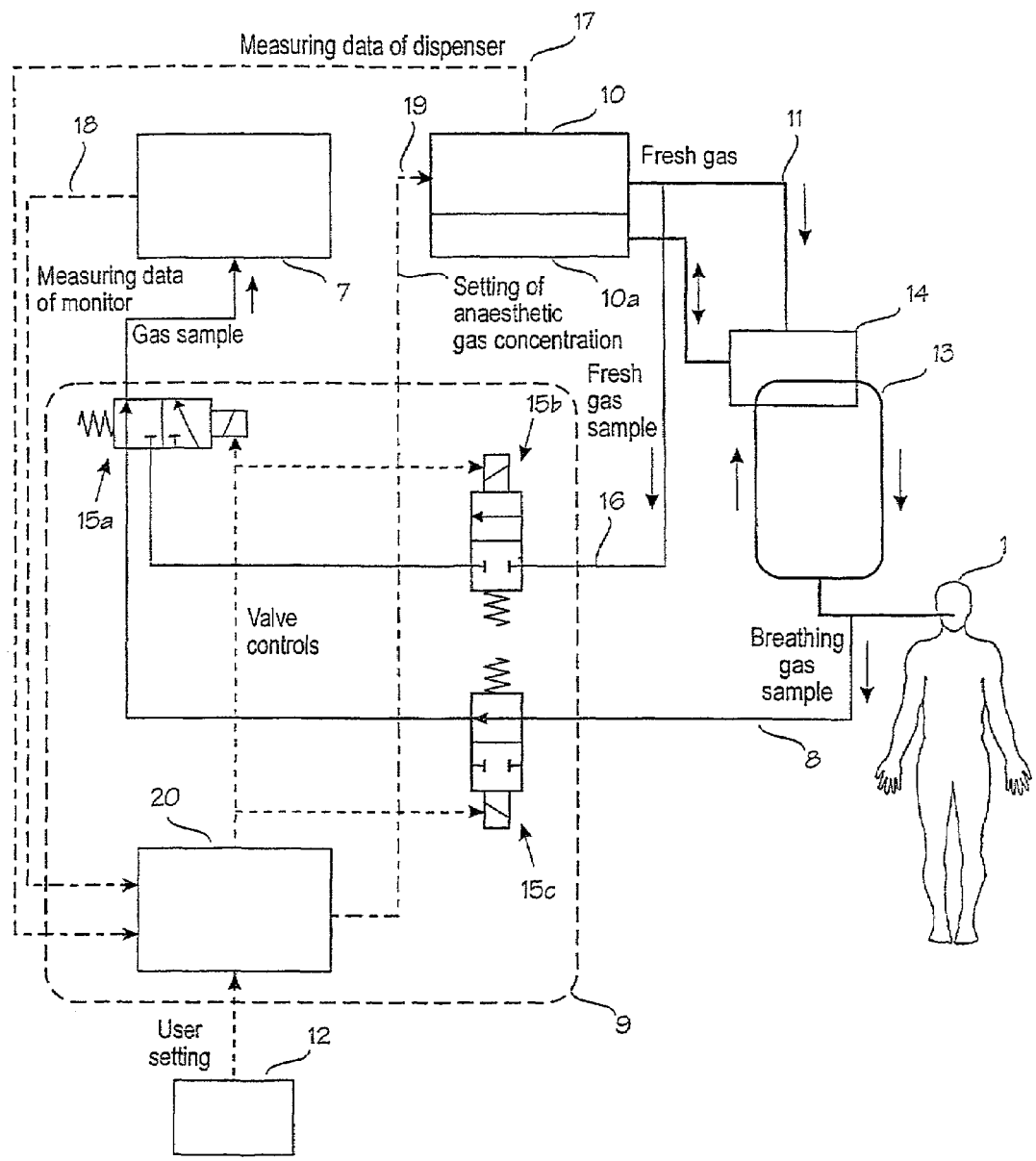
FIG. 3 shows a diagram of an embodiment of the arrangement according to the invention.

FIG. 3 shows schematically a preferred embodiment of an arrangement according to the invention. FIG. 3 uses the same reference numbers as FIG. 2 in the corresponding parts, as in the embodiment of FIG. 3 the invention is applied to the control system of FIG. 2.

In the solution of FIG. 3, a mechanism 15a, 15b, 15c is connected to a separate controller 9, the mechanism changing at suitable intervals sample gas collected by a gas monitor 7 by alternating between the actual gas to be measured, i.e. a breathing gas sample 8, and reference gas, e.g. a fresh gas sample 16. A controller 9 can be a separate controller as in the example of the figure, but it can also be integrated to the monitor or the controllable device. A reference signal is thus given periodically to the gas monitor, the reference signal comprising a fresh gas sample in the example of the figure. Regardless of the gas monitor, the gas dispenser 10 is perfectly aware of the real anaesthetic concentration of the reference gas. The real concentration value 17 of the reference gas given by the gas dispenser and the measuring value 18 of the monitor obtained from the reference gas sample, or reference signal, that is fed to it, are fed by means of e.g. a serial port to a CPU 20 in the controller that compares these two values with each other. If the accuracy of the values is not approximately the same, the controller detects the fault situation of the measuring device 7 and takes a suitable safety measure, e.g. stops setting the gas dispenser 10 concentration 19 and disconnects the control of the controllable device. Opening a safety valve or giving a suitable alarm signal, for example, can also be regarded as safety measures. An alarm signal may be based on e.g. sound or light effect, or both.

A reference signal is thus given periodically to the gas monitor, the reference signal comprising a fresh gas sample in the example of the figure. Regardless of the gas monitor, the gas dispenser 10 is perfectly aware of the real anaesthetic concentration of the reference gas. The real concentration value 17 of the reference gas given by the gas dispenser and the measuring value 18 of the monitor obtained from the reference gas sample, or reference signal, that is fed to it, are fed by means of e.g. a serial port to the controller that compares these two values with each other. If the accuracy of the values is not approximately the same, the controller detects the fault situation of the measuring device 7 and takes a suitable safety measure, e.g. stops setting the gas dispenser 10 concentration 19 and disconnects the control of the controllable device. Opening a safety valve or giving a suitable alarm signal, for example, can also be regarded as safety measures. An alarm signal may be based on e.g. sound or light effect, or both.

A reference signal need not necessarily be a fresh gas sample as in the example of the figure, but also a sample taken from e.g. indoor air or some other gas having a known concentration can be the gas sample forming the reference signal. A reference signal need not necessarily be a gas sample either, but electric measurement can also use a simulated electric signal, for example, as a reference signal. On pressure side, e.g. circuit pressure measured by a ventilator can act as a reference.

A controller and a change-over mechanism of a gas sample must also be planned to take one-fault situations into account. Otherwise a valve malfunction, for example, could lead into a situation in which, when the collecting point of a sample is changed, this does not actually happen, and the real fault situation remains unobserved. In FIG. 3, the malfunction of the actual selector valve 15a is observed by backup valves 15b, 15c. A CPU 20 controls these valves in the corresponding manner as the selector valve 15a. If the selector valve is stuck in either position, the backup valve closes the sample line. Then the gas monitor does not measure any concentration at all and the measuring results do not accord. In addition, a monitor pump creates low pressure to the sample line, which can also be detected from the monitor alarm. Correspondingly, potential leaks can always be discovered from unmatching measuring results. A controller can also be constructed in a way that one-fault situations e.g. in the CPU or controller electronics are detected. If desired, the CPU of the gas dispenser can also be utilized, which CPU supervises the controller operation by means of a serial interface.

The above embodiment is not intended to restrict the invention in any way, but the invention may be modified completely freely within the scope of the claims. Therefore, it is obvious that the arrangement of the invention or its details do not necessarily have to be exactly the same as shown in the figures, but other solutions are possible, too. The invention is by no means restricted to the measurement of anaesthetics only. A similar arrangement can be used e.g. in the checking of carbon dioxide, blood pressure and many other physiological measurements. The main thing is that a known independent reference has to be arranged for the measurement, which reference can be fed automatically to a measuring device belonging to a closed control system.

The invention claimed is:

1. An arrangement for a feedback control system connected to a medical apparatus, the arrangement comprising:
    a controllable device (10);
    a measuring device (7) adapted to measure a measuring value from a measuring point, which measuring value is dependent on the operation of the controllable device (10);
    a controlling device (9);
    a user interface by which the controlling device (9) can be monitored by means of set values;
    wherein the controlling device (9) is adapted to monitor the controllable device (10) on the basis of the measuring values and set values; and
    means (15a, 15b, 15c) for periodically feeding a reference signal (16) to the measuring device, the reference signal having a real, known reference value (17);
    wherein the controlling device (9) is programmed to compare the measuring value (18) obtained from the measuring device (7) based on the reference signal with the real, known reference value (17) of the reference signal;
    wherein the controlling device (9) is programmed to take a safety measure when the measuring value (18) obtained on the basis of the reference signal and the real, known reference value (17) differ substantially from each other.

2. The arrangement of claim 1, wherein the safety measure comprises disconnection of control of the controllable device.

3. The arrangement of claim 1, wherein the safety measure comprises opening of a safety valve.

4. The arrangement of claim 1, wherein the safety measure comprises providing an alarm signal.

5. The arrangement of claim 1, wherein the controllable device (10) comprises one of a gas mixer and ventilator used in patient care, and wherein the measuring device (7) comprises a gas monitor and wherein the controlling device (9) comprises a separate controller.

6. The arrangement of claim 1, wherein the reference signal (16) is a gas sample.

7. The arrangement of claim 6, further comprising means for feeding the reference signal (16) which comprise a selector valve (15a) adapted to periodically send a gas sample used as a reference signal (16) to a gas monitor.

8. The arrangement of claim 7, wherein the gas sample is a fresh gas sample.

9. The arrangement of claim 7, wherein backup valves (15b, 15c) are adapted to control the operation of the selector valve (15a).

10. An arrangement for a feedback control system connected to a medical apparatus, the medical apparatus having a controllable device (10) for controlling a patient care factor, the arrangement comprising:
    a signal responsive control device (9), the control device (9) operable to control the controllable device (10);
    a user interface (12), the user interface (12) coupled to the control device (9) and providing an input signal to the control device (9) to control the controllable device (10) to provide the patient care factor;
    a first means for sampling (8), the first means for sampling (8) providing a patient care factor sample from the medical apparatus;
    means for measuring (7), the means for measuring (7) having an input for receiving a sample and an output coupled to the control device (9) for providing an output signal indicative of a measured value of a sample property;
    means for providing a reference value (17), the means for providing a reference value (17) providing a reference signal indicative of a known value for a sample property that can be measured by the means for measuring (7);
    a second means for sampling (16), the second means for sampling (16) providing a sample exhibiting the sample property, a known value of which is indicated by the reference signal;
    means for switching (15a, 15b, 15c), the means for switching (15a, 15b, 15c) providing the patient care factor sample from the first means for sampling (8) to the means for measuring (7) to cause the means for measuring (7) to provide a first output signal to the control device (9) suitable for use in conjunction with the input signal from the user interface (12) to control the controllable device (10),
    the means for switching (15a, 15b, 15c) being switchable to provide the property exhibiting sample from the second means for sampling (16) to the means for measuring (7) to cause the means for measuring (7) to provide a second output signal; and
    a comparator for receiving the reference signal and the second output signal from the means for measuring (7), the comparator for comparing the reference signal and the second output signal to determine the operative condition of the means for measuring (7).

11. The arrangement according to claim 10, wherein the means for measuring is a gas monitor and wherein the first means for sampling provides a gas sample and the second means for sampling provides a gas sample.

12. The arrangement according to claim 10, wherein the means for providing a reference value provides a reference signal obtained from the controllable device (10).

13. The arrangement according to claim 10, wherein the means for providing a reference value provides a reference signal obtained from a source that is independent of the controllable device (10).

14. The arrangement according to claim 10, wherein the means for switching (15a, 15b, 15c) comprises a valve connected to the first and second means for sampling.

15. The arrangement according to claim 14, further comprising at least one backup valve (15b, 15c) for the valve connected to the first and second means for sampling.

16. The arrangement according to claim 10, wherein the medical apparatus comprises anesthesia administration apparatus and wherein the controllable device comprises a gas dispenser.

17. The arrangement according to claim 11, wherein the medical apparatus comprises anesthesia administration apparatus and wherein the controllable device comprises a gas dispenser.

18. The arrangement according to claim 16, wherein the medical apparatus comprises anesthesia administration apparatus and wherein the controllable device comprises a gas dispenser, and wherein the means for sampling provides a patient breathing gas sample, wherein the second means for sampling provides a fresh gas sample and wherein the means for providing a reference value provides a gas concentration reference signal.

19. The arrangement according to claim 10, further comprising means for instituting safety measures when the values of the reference signal and the second output signal differ by a predetermined amount.

20. The arrangement according to claim 19, wherein the means for instituting safety measures is further defined as instituting a safety measure comprising disconnection of control of the controllable device (10) responsive to the comparison made by the comparator.

21. The arrangement according to claim 19, wherein the medical apparatus has a safety valve and wherein the means for instituting safety measures is further defined as instituting a safety measure comprising opening the safety valve responsive to the comparison made by the comparator.

22. The arrangement according to claim 19, wherein the medical apparatus comprises an alarm and wherein the means for instituting safety measures comprises providing an alarm signal responsive to the comparison made by the comparator.

23. An arrangement for a feedback control system connected to a medical apparatus, the medical apparatus having a gas dispenser for controlling a patient care factor, the arrangement comprising:

a controller, the controller operable to control the gas dispenser;

a user interface, the user interface coupled to the controller and providing an input signal to the controller to control the gas dispenser to provide the patient care factor;

a first means for sampling, the first means for sampling providing a patient care factor sample from the medical apparatus;

gas monitor, the gas monitor having an input for receiving a sample and an output coupled to the controller for providing an output signal indicative of a measured value of a sample property;

means for providing a reference value, the means for providing a reference value providing a reference signal indicative of a known value for a sample property that can be measured by the gas monitor;

a second means for sampling, the second means for sampling providing a sample exhibiting the sample property, a known value of which is indicated by the reference signal;

means for switching, the means for switching providing the patient care factor sample from the first means for sampling to the gas monitor to cause the gas monitor to provide a first output signal to the controller suitable for use in conjunction with the input signal from the user interface to control the gas dispenser;

the means for switching being switchable to provide the property exhibiting sample from the second means for sampling to the gas monitor to cause the gas monitor to provide a second output signal; and a comparator for receiving the reference signal and the second output signal from the gas monitor, the comparator for comparing the reference signal and the second output signal to determine the operative condition of the gas monitor.

* * * * *